US012622736B2

(12) United States Patent
Maier

(10) Patent No.: US 12,622,736 B2
(45) Date of Patent: May 12, 2026

(54) ELECTROSURGICAL SYSTEM AND METHOD FOR OPERATION THEREOF

(71) Applicant: Erbe Elektromedizin GmbH, Tuebingen (DE)

(72) Inventor: Philipp Maier, Tuebingen (DE)

(73) Assignee: Erbe Elektromedizin GmbH, Tuebingen (DE)

( * ) Notice: Subject to any disclaimer, the term of this patent is extended or adjusted under 35 U.S.C. 154(b) by 280 days.

(21) Appl. No.: 18/383,786

(22) Filed: Oct. 25, 2023

(65) Prior Publication Data

US 2024/0138897 A1 May 2, 2024

(30) Foreign Application Priority Data

Oct. 28, 2022 (EP) .................................... 22204530

(51) Int. Cl.
| | |
|---|---|
| *A61B 18/16* | (2006.01) |
| *A61B 18/12* | (2006.01) |
| *A61B 18/00* | (2006.01) |

(52) U.S. Cl.
CPC .......... *A61B 18/1206* (2013.01); *A61B 18/16* (2013.01); *A61B 2018/0072* (2013.01); *A61B 2018/00767* (2013.01); *A61B 2018/00875* (2013.01); *A61B 2018/124* (2013.01); *A61B 2018/1253* (2013.01); *A61B 2018/126* (2013.01); *A61B 2018/128* (2013.01); *A61B 2018/1293* (2013.01); *A61B 2018/165* (2013.01)

(58) Field of Classification Search
CPC ................ A61B 18/1206; A61B 18/16; A61B 2018/124; A61B 2018/1293; A61B 2018/165
See application file for complete search history.

(56) References Cited

U.S. PATENT DOCUMENTS

| | | |
|---|---|---|
| 6,275,786 B1 | 8/2001 | Daners |
| 11,376,059 B2 | 7/2022 | Fahsing |

(Continued)

FOREIGN PATENT DOCUMENTS

| | | |
|---|---|---|
| DE | 19714972 A1 | 10/1998 |
| DE | 102016220157 A1 | 4/2018 |

(Continued)

*Primary Examiner* — Sean W Collins
(74) *Attorney, Agent, or Firm* — Blank Rome LLP

(57) ABSTRACT

A supply apparatus for an electrosurgical system as well as an electrosurgical system having a supply apparatus. In addition to a generator, the supply apparatus has a measurement signal source that is able to provide a measurement signal (XM) in form of an alternating voltage and/or an alternating current. An impedance parameter (P) resulting from the measurement signal (XM) can be evaluated. A switch device of supply apparatus can be switched between multiple switch conditions (C1-C5). In the different switch conditions (C1-C5) different evaluation functions can be realized by means of the evaluation unit (50). The measurement signal source can apply a measurement signal to a treatment current path (B) at a working connection of supply apparatus as well as to a neutral current path (N) between neutral connections of supply apparatus. In doing so, by means of the measurement signal (XM), treated tissue can be analyzed as well as a contact between neutral electrode and the patient can be checked or monitored.

18 Claims, 6 Drawing Sheets

(56)                    References Cited

U.S. PATENT DOCUMENTS

Figure 1:
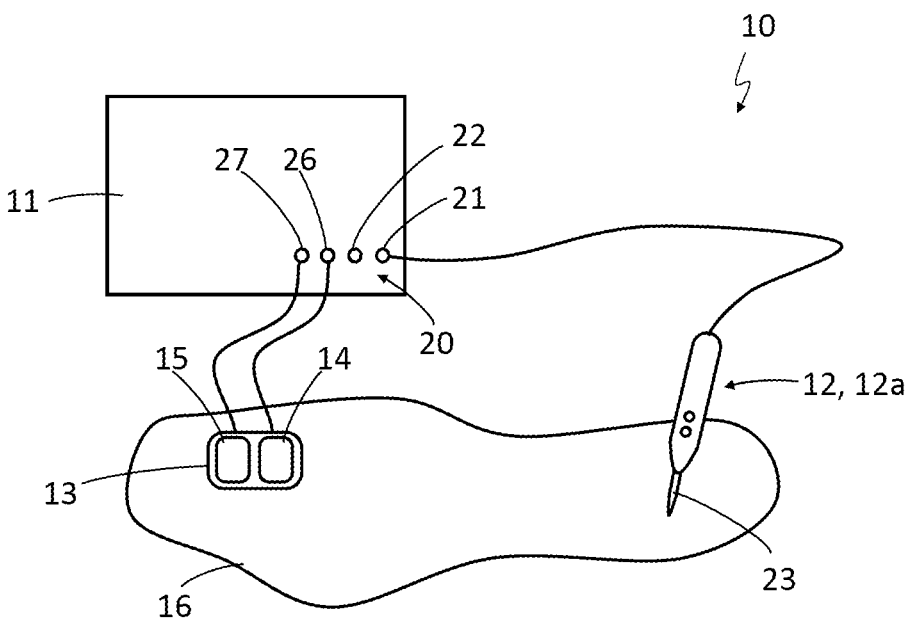

| | | | |
|---|---|---|---|
| 2006/0015095 A1 | 1/2006 | Desinger et al. | |
| 2014/0074084 A1 | 3/2014 | Engeberg et al. | |
| 2016/0074093 A1* | 3/2016 | Shimizu | A61B 18/1206 |
| | | | 606/35 |
| 2018/0221085 A1* | 8/2018 | Blanck | A61N 1/3956 |
| 2021/0401495 A1* | 12/2021 | Qian | A61B 18/1492 |
| 2022/0226035 A1* | 7/2022 | Møller | A61B 18/16 |

FOREIGN PATENT DOCUMENTS

| | | | |
|---|---|---|---|
| DE | 102018114482 A1 | 4/2019 | |
| EP | 0813387 A1 | 12/1997 | |
| EP | 1511534 B1 | 7/2011 | |
| EP | 2200527 B1 | 11/2014 | |
| EP | 3496638 A1 | 6/2019 | |
| WO | 9627327 A1 | 9/1996 | |
| WO | 0232335 A1 | 4/2002 | |
| WO | 2012151493 A2 | 11/2012 | |
| WO | 2018029154 A1 | 2/2018 | |
| WO | 2020198796 A1 | 10/2020 | |

* cited by examiner

ELECTROSURGICAL SYSTEM AND METHOD FOR OPERATION THEREOF

CROSS-REFERENCE TO RELATED APPLICATION

This application claims priority to European Patent Application No. 22204530.4, filed Oct. 28, 2022, the entirety of which is incorporated by reference herein.

The invention refers to an electrosurgical system as well as a method for operation thereof.

In electrosurgical systems it is known to analyze tissue by means of impedance spectroscopy, e.g. to distinguish healthy tissue from tumor tissue. For this purpose, the impedance of the tissue is determined and evaluated by means of a measurement current between two electrodes.

Such a method is known from EP 0 813 387 A1, for example. Between multiple electrodes of an instrument of an electrosurgical system either a measurement voltage or a treatment voltage that is higher compared with the measurement voltage can be applied. By means of the measurement voltage impedance measurements can be carried out for tissue identification. By means of the treatment voltage tissue can be treated. In a supply apparatus for supply of the instrument with the measurement voltage or the treatment voltage a switch device can be present in order to be able to switch between an energy source for the measurement voltage and an energy source for the treatment voltage.

EP 1 511 534 B1 describes a device for electrosurgical obliteration of body tissue. The device has a supply apparatus to which multiple electrodes are connected. By means of a high frequency generator of the supply apparatus, a current flow is created between two electrodes respectively in order to coagulate the tissue. By means of a measurement device the impedance between two electrodes can be determined and from the number of present electrodes at least two active electrodes can be selected based on the impedance measurement.

The electrosurgical system according to WO 2012/151 493 A2 comprises a supply apparatus and an instrument connected thereto. By means of a switch, an evaluation device for impedance analysis of the tissue or a generator for producing a high-frequent treatment voltage can be selectively connected to the instrument. By means of the evaluation device, frequencies are identified that decrease the impedance and thus increase the conductance of the tissue. Subsequently, the treatment voltage is applied to the instrument at the identified frequencies.

An impedance measurement device in an electrosurgical system is in addition described in DE 10 2016 220 157 A1. Based on the impedance measurement at different frequencies, a condition of the treated tissue can be determined. For example, an undesired carbonization of tissue or sticking of tissue on the electrodes of the electrosurgical instrument shall be avoided.

DE 10 2018 114 482 A1 as well as DE 197 14 972 A1 describe an electrosurgical system having a monopolar instrument and a neutral electrode that are connected to a supply apparatus. By means of an impedance measurement, a neutral electrode type is determined in DE 10 2018 114 482 A1, whereas DE 197 14 972 A1 proposes to monitor the contact of the neutral electrode on the body of the patient based on a measured tissue impedance. In both applications the measurement of the tissue impedance is carried out at multiple frequencies.

EP 3 496 638 A1 discloses an electrosurgical system having a measurement unit. The electrosurgical system has a supply apparatus and at least two electrodes connected to the supply apparatus and between which an alternating voltage for treatment of tissue can be applied. In addition, it is possible to apply a measurement voltage between the electrodes at a frequency being different than the treatment alternating voltage and to determine therefrom a tissue characteristic of the tissue between the electrodes.

Starting from the prior art, it can be considered as object of the present invention to provide an improved supply apparatus as well as an improved electrosurgical system that allows a tissue analysis as well as contact of a neutral electrode on the patient with simple and economical configuration.

This object is solved by embodiments described herein.

Supply apparatuses in accordance with embodiments of the present invention is configured and provided for use in an electrosurgical system. It comprises multiple apparatus connections for connection of an electrosurgical instrument and for optional connection of a neutral electrode. Two neutral connections for connecting a neutral electrode and at least one working connection for one working electrode of an electrosurgical instrument respectively are apparatus connections. If the supply apparatus comprises at least one working connection bipolar (or also other multipolar) instruments can be connected to the working connections. For connecting a monopolar instrument one working connection for the working electrode of the monopolar instrument is sufficient. In this case the neutral connections for connecting the neutral electrode are used, which are not needed in case of using a bipolar instrument.

The supply apparatus comprises in addition a generator for providing a generator voltage and/or a generator current. The generator voltage is a high frequency voltage and/or the generator current is a high frequency current. The frequency of the generator voltage and/or the generator current is particularly at least 200 kHz. The generator current or the generator voltage are provided to the at least one working electrode of an electrosurgical instrument in order to treat biological tissue, e.g. to coagulate or to cut biological tissue.

The supply apparatus comprises in addition a measurement signal source for providing a measurement signal. The measurement signal is an alternating voltage signal or an alternating current signal having preferably alternating polarity. Accordingly, the measurement signal source can be a voltage source or a current source. The measurement signal has a measurement frequency that is preferably in a range up to 100 MHz at most. As an option, the measurement frequency can be minimum 10 Hz, minimum 50 Hz or minimum 100 Hz. The measurement frequency is particularly variable. Preferably two or more different measurement frequencies can be selected or set for the measurement signal.

The supply apparatus comprises in addition a measurement device for measurement of an impedance parameter that describes an impedance between two of the provided apparatus connections respectively, for which the measurement signal is provided. Between these selected apparatus connections, a measurement voltage is applied or a measurement current flows. Depending from whether a monopolar or bipolar instrument is used, two apparatus connections are electrically conductively connected with one another via a first working electrode, the tissue of a patient and a second working electrode (bipolar instrument) or electrically conductively connected with one another via at least one working electrode, the tissue of a patient and a neutral electrode (monopolar instrument). In both cases the impedance parameter depends inter alia from the impedance of the tissue of the patient.

For measurement of at least one current and/or at least one voltage, the measurement device can comprise one or more current sensors and/or voltage sensors.

The supply apparatus comprises in addition a switch device. The switch device can be switched between multiple switch conditions and according to the example, at least between a first switch condition and a second switch condition.

In the first switch condition the switch device connects the measurement signal source on one side with the first of the two neutral connections and on the other side with the second of the two neutral connections. Thus, a measurement voltage can be applied between the two neutral connections or with the neutral electrode being connected, a measurement current can flow from the first neutral connection to the second neutral connection through the neutral electrode or vice versa.

In the first switch condition the measurement signal source is separated from the at least one working connection so that a working electrode connected to the at least one working connection is not provided with the measurement signal.

In the second switch condition, however, the measurement signal source is electrically connected with the at least one working connection. The measurement signal is provided to a working electrode of a connected electrosurgical instrument. In case of a bipolar instrument, based on the measurement signal a current can flow from the one working electrode via the tissue to the other working electrode and from there back to the measurement signal source, while in case of a connected monopolar instrument as well as a connected neutral electrode based on the measurement signal a current can flow from the at least one working electrode via the tissue of the patient to the neutral electrode and from there back to the measurement signal source. Independent from the type of the used instrument, a closed current circuit comprising the measurement signal source is provided via the at least one working electrode and the tissue of the patient in the second switch condition.

The supply apparatus comprises in addition an evaluation unit communicatively connected with the measurement device. The evaluation unit is configured to evaluate the measured impedance parameter. Depending from the evaluation result, the possibility exists to control the supply apparatus and/or to provide information to the user, for example a surgeon, by a user interface of the supply apparatus.

Via the switch device the measurement signal of the measurement signal source can thus create a current flow through the neutral electrode (first switch condition) or a current flow via a working electrode, a tissue to be treated and via an additional working electrode or alternatively a connected neutral electrode back to the measurement signal source (second switch condition). The measurement signal source is thus usable for monitoring or checking a contact between the neutral electrode and a patient (first switch condition) as well as for determining the condition and/or the type of a tissue to be treated of a patient (second switch condition).

Accordingly, by the measurement signal source an impedance spectroscopy for determination of the condition and/or the type of a treated tissue can be carried out independent from the generator voltage and/or the generator current and the correct contact or the correct attachment of the neutral electrode to the patient can be checked and/or monitored. For example, during use of the supply apparatus it can repeatedly switch between the first switch condition and the second switch condition, so that repeatedly the treated tissue can be analyzed as well as the correct contact of the neutral electrode can be checked and monitored. Separate voltage or current sources for the impedance spectroscopy on one hand and the monitoring of the contact of a neutral electrode on the other hand are not necessary.

In a preferred embodiment the supply apparatus is suitable and configured for the connection of a monopolar instrument as well as for connection of a bipolar instrument.

The supply apparatus has a first working connection for connecting a working electrode of a monopolar instrument. Optionally the supply apparatus can comprise a second working connection for connection of a second working electrode in addition to the first working connection. A bipolar instrument having a first working electrode and a second working electrode can be connected to the first working connection and the second working connection. The supply apparatus is then suitable for operation of monopolar as well as for operation of bipolar instruments.

In a preferred embodiment the measurement signal source is configured as alternating voltage source and provides a load-independent alternating voltage in form of a measurement voltage as measurement signal. Alternatively, an alternating current source can be used as a measurement signal source. In both cases the alternating voltage or the alternating current can be provided at different measurement frequencies.

In the first switch condition the evaluation device is particularly configured to check or monitor an electrical contact between a patient and a neutral electrode connected to the two neutral connections based on the measured impedance parameter. For this purpose, the impedance between the two neutral connections is determined based on the impedance parameter. The impedance can be determined at one single or at multiple different measurement frequencies of the measurement signal.

Preferably the neutral electrode connected to the two neutral connections comprises two electrically conductive electrode areas that are not directly electrically connected with one another inside the neutral electrode. Therefore, the electrode areas of the neutral electrode can have different electrical potentials. They are electrically not short-circuited or connected in low ohmic manner inside the neutral electrode. An electrical connection between the electrode areas is achieved via the patient during intended use of the neutral electrode. The neutral electrode is particularly attached, particularly adhesively attached, on the skin of the patient at a suitable position.

Due to the determination of the impedance between the two neutral connections, a correct arrangement with sufficiently high conductance between the neutral electrode and the patient can be checked and monitored. An insufficient contact can be indicated to a user of the supply apparatus by a suitable user interface. In addition or as an alternative, the operation of the supply apparatus can be interrupted, if it is determined that the electrically conducting contact between the neutral electrode and the patient is insufficient during use of the supply apparatus. In both variants tissue damages, due to too high current densities in the area of the neutral electrode, can be avoided.

It is in addition advantageous, if the evaluation unit is configured to determine a tissue type based on the measured impedance parameter in the second switch condition. In the second switch condition particularly an evaluation of the impedance can be carried out that inter alia depends on the treated tissue, i.e. particularly on the condition and/or the type of the tissue. The impedance determination in the second switch condition can be carried out at one or multiple measurement frequencies of the measurement signal. In doing so, it is possible to determine a tissue type and/or a condition of the treated tissue with which the at least one working electrode of the instrument is in electrically conducting contact.

It is preferred, if the switch device separates the generator electrically from the measurement signal source and/or the apparatus connections in the first switch condition and the second switch condition, so that no generator current flows to the measurement signal source and/or the apparatus connections.

In a preferred embodiment the generator is configured or controlled so that the generator does not create a generator voltage and/or a generator current in the first switch condition and in the second switch condition. No generator voltage is applied to the at least one working connection and/or no current flow of a generator current is allowed via the at least one working connection to a working electrode connected thereto. In doing so, it is avoided that a generator voltage and/or a generator current interferes the evaluation of the impedance parameter in the first switch condition and the second switch condition.

Preferably the switch device connects the measurement signal source on one side electrically with the at least one first working connection and on the other side with the two neutral connections in the second switch condition. The two neutral connections are connected with one another in a low ohmic manner or are short-circuited inside the supply apparatus by the switch device in the second switch condition. The two neutral connections, therefore, have substantially the same electrical potential.

In a preferred embodiment the switch device can be switched in an optional third switch condition, in which the switch device electrically connects the generator on one side with the at least one working connection and electrically connects the generator on the other side with the neutral connections. With a monopolar instrument connected and a neutral electrode connected, in this third switch, due to the generator voltage and/or the generator current condition a current flow is allowed to the working electrode of the instrument, from there through the tissue being in electrically conducting contact with the working electrode and via the neutral electrode again back to the supply apparatus. This third switch condition serves particularly the treatment of tissue by a monopolar instrument, e.g. the coagulation or cutting of tissue.

The evaluation unit is particularly configured to check a current flow through the two neutral connections in the third switch condition caused by the generator voltage and/or the generator current, e.g. in order to compare a first current from the first neutral connection at a second current from the second neutral connection with one another. In this comparison one or multiple current parameters of the first current and the second current can be compared with each other, e.g. an amplitude and/or an absolute value and/or a phase position.

In the third switch condition the measurement signal source can, at least during periods, provide a measurement signal. Particularly, the evaluation unit is configured so that it can also evaluate the impedance parameter detected at the neutral connections during a monopolar treatment current flow in order to check or monitor the transition impedance or the electrical contact between the neutral electrode and the patient. The measurement frequency is thereby sufficiently different from the generator frequency of the generator voltage or the generator current. An insufficient electrical contact (too high transition impedance) between the neutral electrode and the patient can also be recognized during an activation of the generator, e.g. caused by an at least partial detachment of the neutral electrode from the patient.

In a preferred embodiment the measurement device comprises a frequency-dependent impedance circuit that can comprise a parallel oscillating circuit or that can be a parallel oscillating circuit. For example, the parallel oscillating circuit can be configured from a parallel inductance and two series capacitors. The frequency-dependent impedance circuit (e.g. the parallel oscillating circuit) connects the first neutral connection with the second neutral connection.

Preferably the switch device comprises one or more controllable switches that separate the frequency-dependent impedance circuit from the first neutral connection and/or from the second neutral connection, if the switch device is in the first switch condition and/or the second switch condition. Preferably at least or exclusively in the third switch condition an electrical connection between the frequency-dependent impedance circuit and the first neutral connection and/or the second neutral connection is established.

It is advantageous, if in the third switch condition the measurement signal source is configured or controlled in a manner so that the measurement frequency of the measurement signal varies in a predefined frequency range. In doing so, it is particularly possible to determine a frequency at which the frequency-dependent impedance circuit comprises a local or global impedance maximum.

Preferably the switch device can electrically connect the measurement signal source on one side with the first working connection and on the other side with the second working connection in an optional fourth switch condition. The fourth switch condition is provided for the use of a bipolar instrument and is so-to-speak used in analog manner to the second switch condition during use of a monopolar instrument. The evaluation unit is configured to determine the condition and/or the type of the tissue with which the working electrodes of the connected instrument are in electrically conducting contact based on the measured impedance parameter in the fourth switch condition.

Preferably the switch device can connect the generator with the first and the second working connection in an optional fifth switch condition and can separate the measurement signal source from the working connections. The fifth switch condition is provided for the use of a bipolar instrument with generator current.

Particularly the measurement signal source is configured or is controlled so that it does not produce a measurement signal in the fifth switch condition.

For controlling the switch device and optionally the measurement signal source and/or the generator, the supply apparatus can have a control unit. The control unit and particularly the evaluation unit can be realized integrated in one single component (particularly IC).

The labeling of features, particularly of components and switch conditions, by a numeral "first", "second", etc. exclusively serves the distinction of features and does not implicit any sequence or prioritization. For example, a fifth switch condition can be present, even if no fourth switch condition exists.

The invention also refers to an electrosurgical system comprising a supply apparatus according to any of the embodiments described above. In addition, an electrosurgical instrument as well as optionally a neutral electrode, in case the electrosurgical instrument is a monopolar instrument, are in addition part of the electrosurgical system. If a bipolar instrument is part of the electrosurgical system, the bipolar instrument is connected to a first working connection and a second working connection of the supply apparatus. If a monopolar instrument as well as a neutral electrode are part of the electrosurgical system, the monopolar instrument is connected to the working connection or to one of the present working connections and the neutral electrode is connected to the first neutral connection and the second neutral connection.

Figure 2:
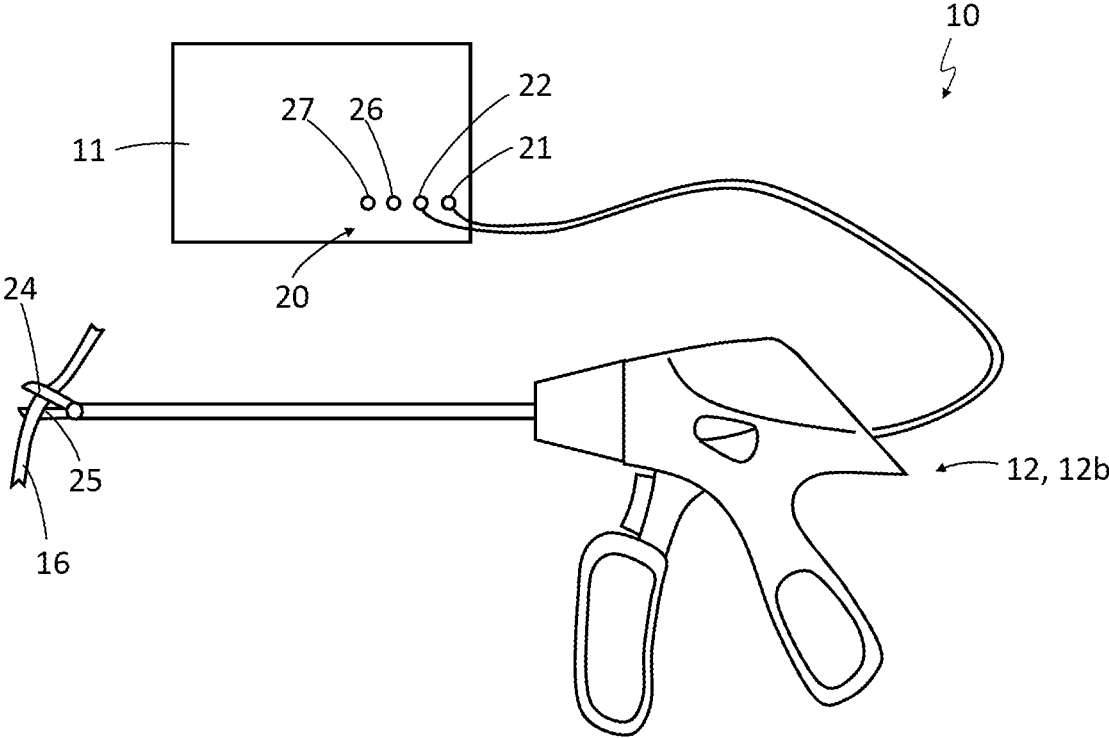
Figure 3:
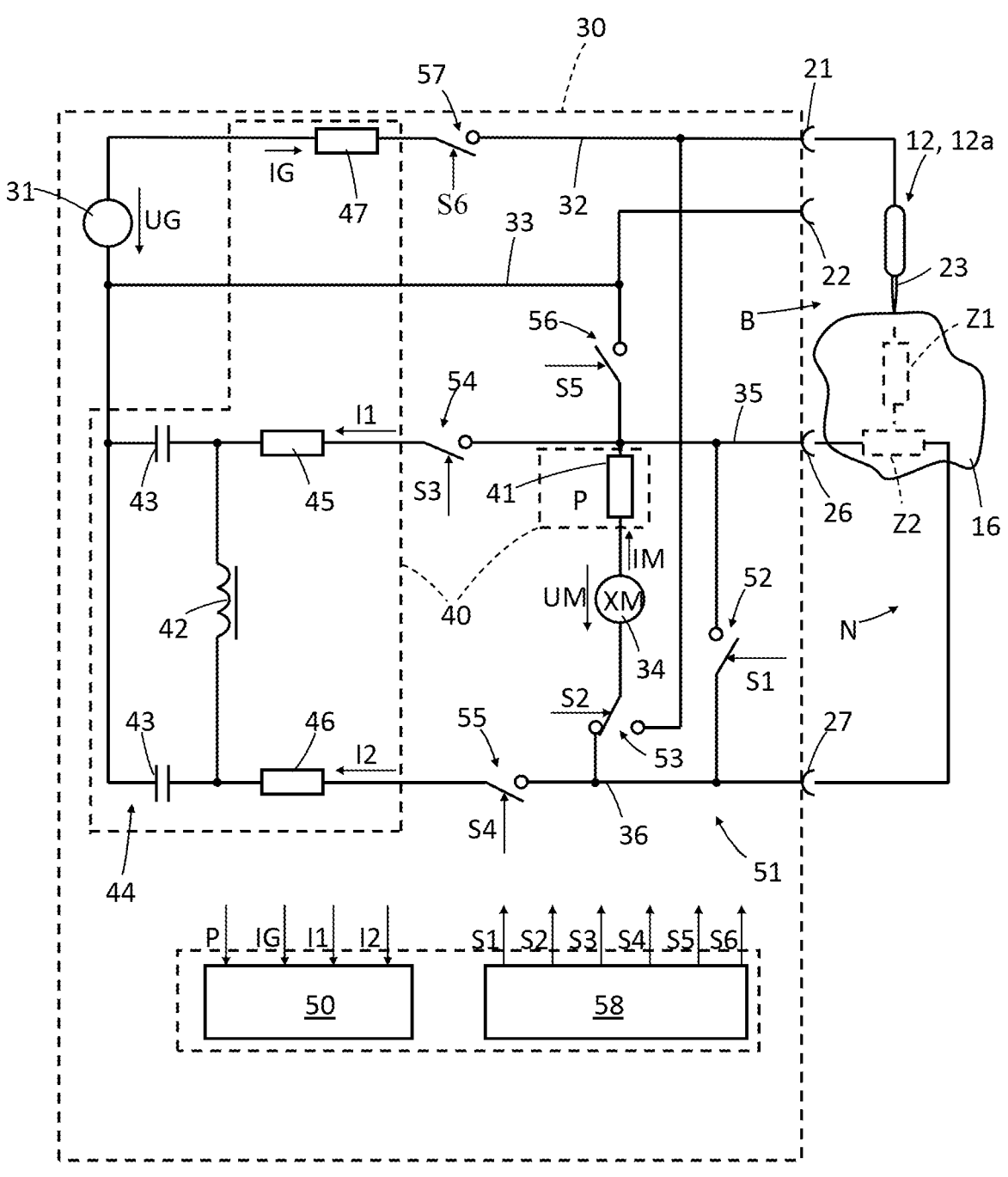
Figure 4:
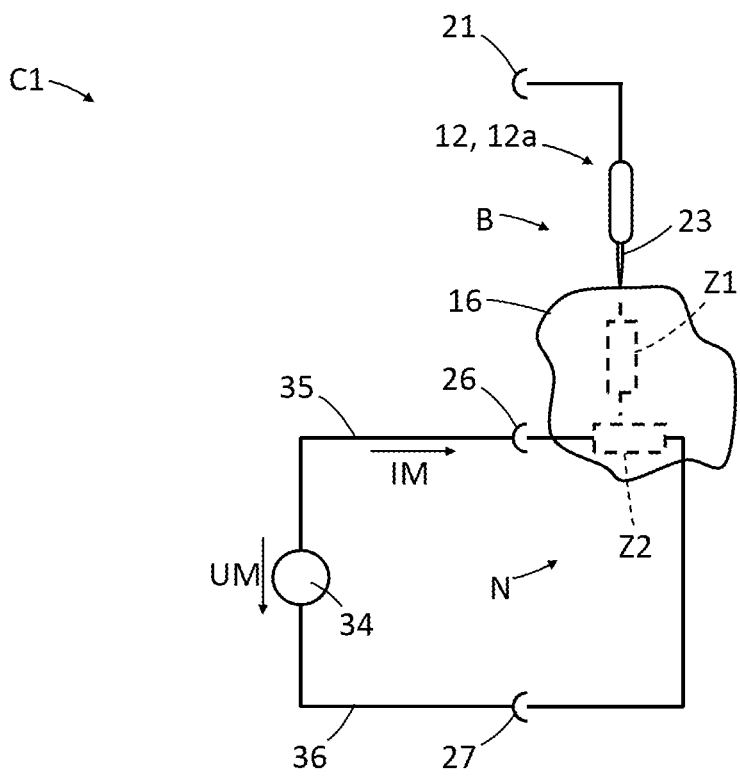
Figure 5:
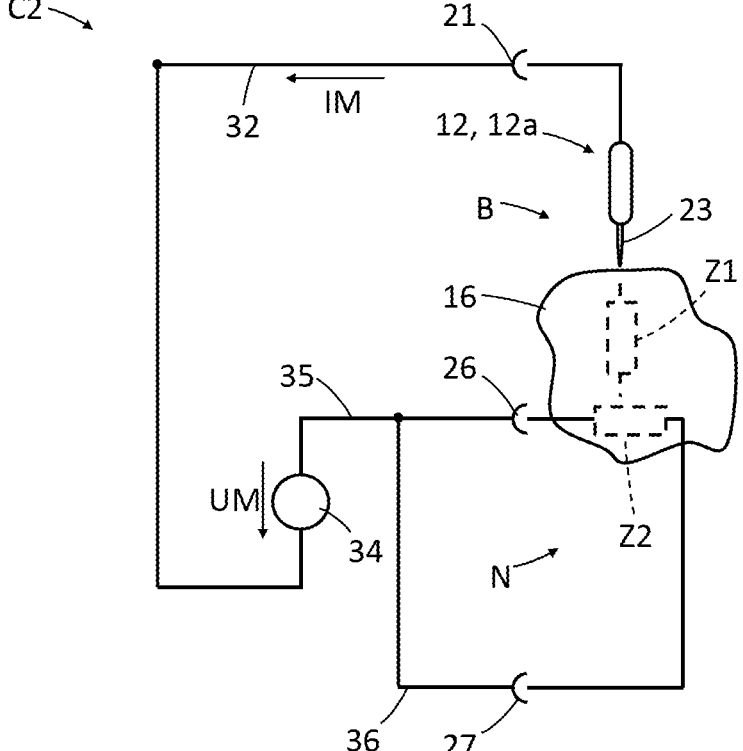
Figure 6:
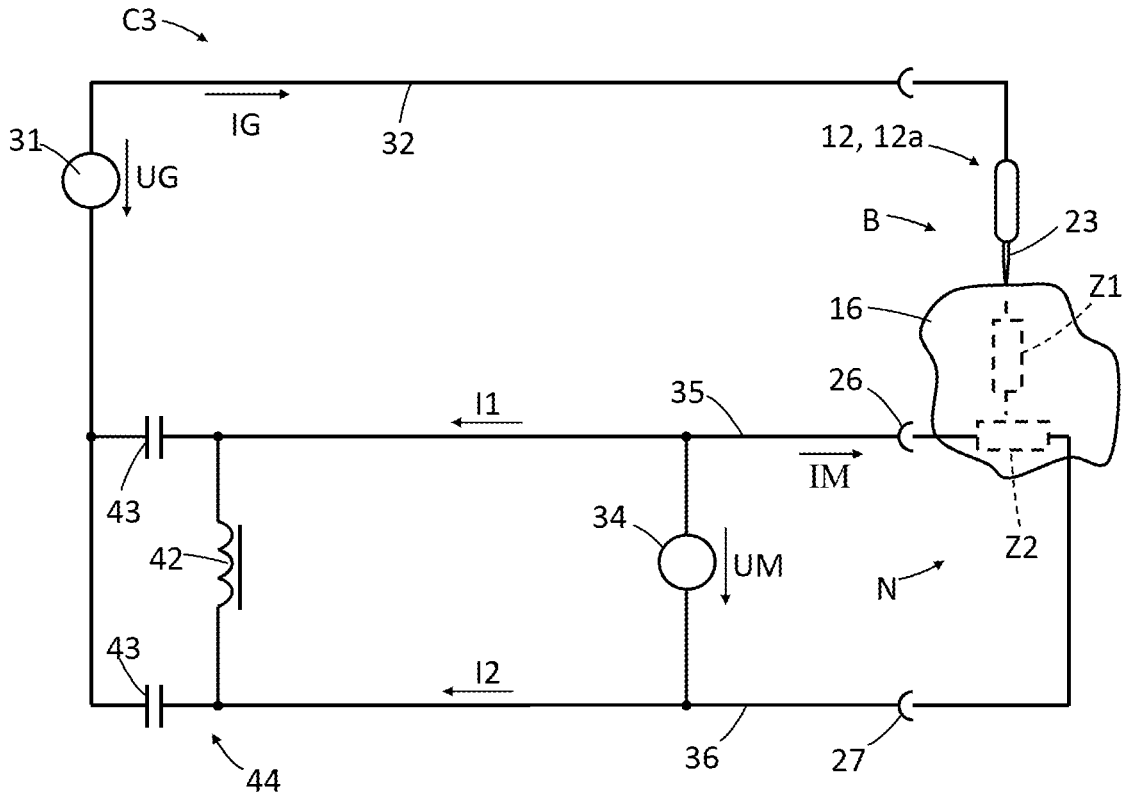
Figure 7:
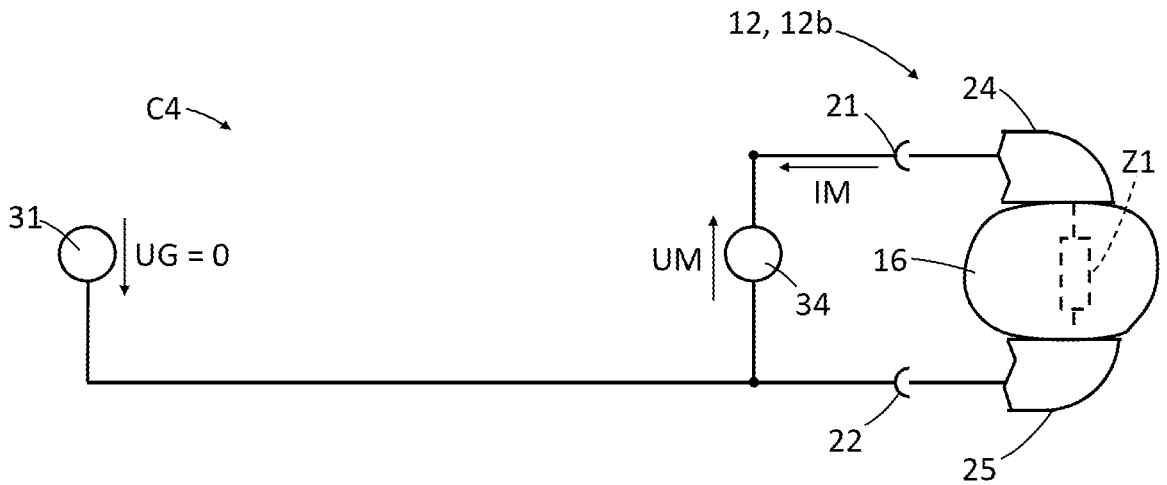
Figure 8:
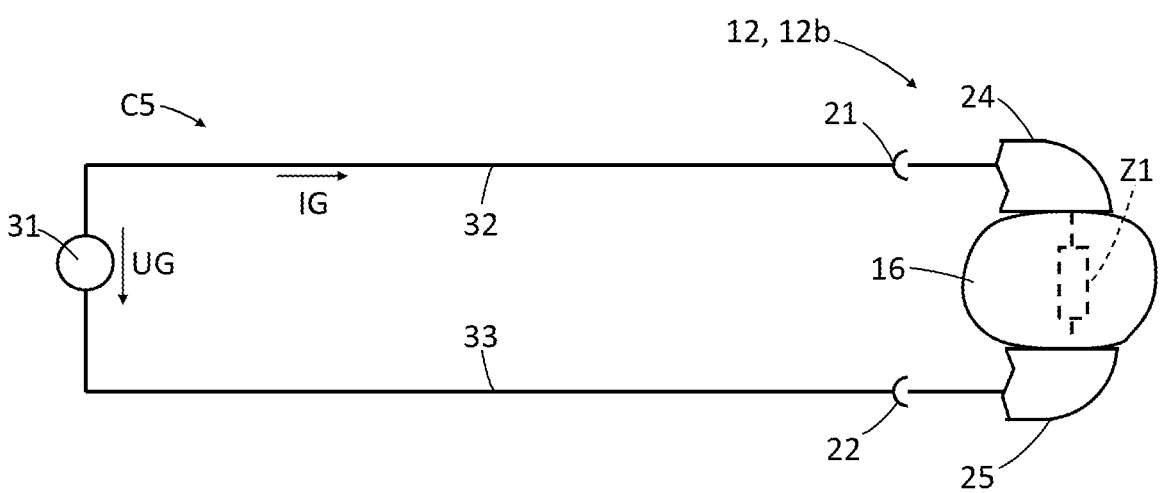
Figure 9:
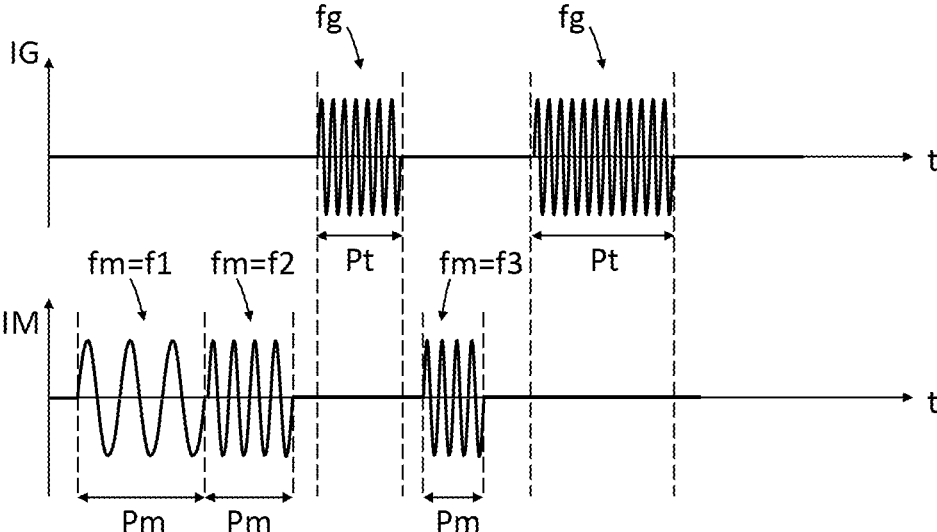
Figure 10:
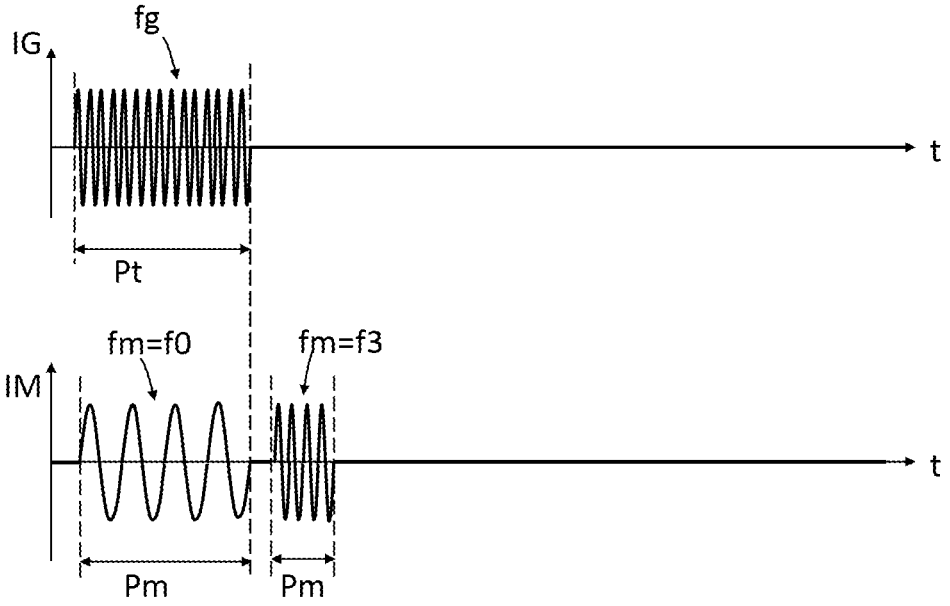
Figure 11:
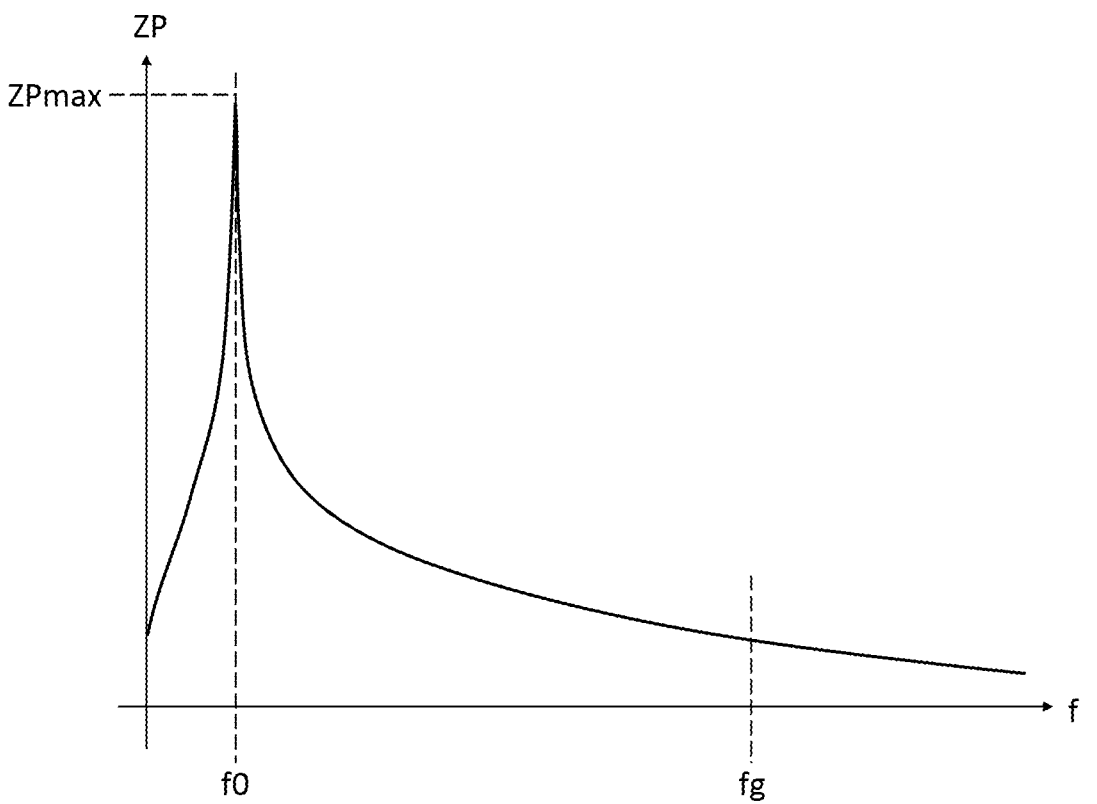

Advantageous embodiments of the invention are derived from the dependent claims, the description and the drawing. In the following, preferred embodiments of the invention are explained in detail based on the attached drawing. The drawing shows:

FIG. 1 a principle illustration of an embodiment of an electrosurgical system comprising a supply apparatus, a monopolar instrument as well as a neutral electrode, FIG. 2 a principle illustration of another embodiment of the electrosurgical system comprising a supply apparatus as well as a bipolar instrument, FIG. 3 an embodiment of an operating circuit of the supply apparatus of FIGS. 1 and 2 in form of a block diagram, whereby the operating circuit comprises a generator, a measurement signal source, a measurement device, an evaluation unit as well as a switch device, FIG. 4 an equivalent circuit diagram of the operating circuit of FIG. 3 in a first switch condition of the switch device, FIG. 5 an equivalent circuit diagram of the operating circuit of FIG. 3 in a second switch condition of the switch device, FIG. 6 an equivalent circuit diagram of the operating circuit of FIG. 3 in a third switch condition of the switch device, FIG. 7 an equivalent circuit diagram of the operating circuit of FIG. 3 in a fourth switch condition of the switch device, FIG. 8 an equivalent circuit diagram of the operating circuit of FIG. 3 in a fifth switch condition of the switch device, FIG. 9 a schematic exemplary illustration of a temporal progress of a generator current and a measurement current of the operating circuit of the supply apparatus in the first and/or second and/or fourth and/or fifth switch condition, FIG. 10 a schematic exemplary illustration of a temporal progress of a generator current and a measurement current of the operating circuit of the supply apparatus in the third switch condition and FIG. 11 an exemplary absolute value progress of an impedance of a frequency-dependent impedance circuit depending on the frequency.

In FIGS. 1 and 2 embodiments of an electrosurgical system 10 are illustrated by way of example. The electrosurgical system 10 has a supply apparatus 11 corresponding to an embodiment according to the invention. An electrosurgical instrument 12 is connected to the supply apparatus 11. The electrosurgical instruments shown in FIGS. 1 and 2 are configured for the open surgical use. Alternatively to this, the electrosurgical instrument 12 could also be configured for the endoscopic or minimally invasive use.

The electrosurgical instrument 12 can be a monopolar instrument 12a (FIG. 1) or a bipolar instrument 12b (FIG. 2). When using a monopolar instrument 12a, the electrosurgical system comprises in addition a neutral electrode 13.

In the embodiment illustrated here the neutral electrode 13 comprises an electrically conductive first electrode area 14 as well as an electrically conductive second electrode area 15. The two electrode areas 14, 15 are not directly electrically connected with one another in low ohmic manner inside the neutral electrode 13, so that they can have different electrical potentials. During use the neutral electrode 13 is attached to a patient to be treated, so that the electrode areas 14, 15 are electrically conductively connected to the patient. For example, the neutral electrode 13 can be adhesively attached on the skin of a patient. An electrical connection between the two electrode areas 14, 15 is then indirectly established via the patient. In this condition a current flow between the two electrode areas 14, 15 is indirectly possible via the patient.

The electrosurgical system is configured to treat biological tissue 16 of a patient by the electrosurgical instrument 12. The biological tissue 16 can be organ tissue, muscle tissue, fat tissue, skin tissue, vessels or other biological tissue 16 of the patient. For example, by the electrosurgical instrument 12, the tissue 16 can be coagulated and/or cut.

For connection of the electrosurgical instrument 12 (monopolar instrument 12a or bipolar instrument 12b) as well as for connection of the neutral electrode 13, supply apparatus 11 comprises multiple electrical apparatus connections 20 in the embodiment. The number of apparatus connections 20 can vary. The supply apparatus 11 has at least one working connection for connecting the electrosurgical instrument 12. In the illustrated embodiment the supply apparatus 11 comprises at least two working connections, namely a first working connection 21 as well as a second working connection 22 so that monopolar instruments 12a as well as bipolar instruments 12b can be connected. The working electrode 23 of the monopolar instrument 12a can be connected to the first working connection 21. When using a bipolar instrument 12b, a first working electrode 24 can be connected to the first working connection 21 and a second working electrode 25 can be connected to the second working connection 22.

In addition, a first neutral connection 26 for electrical connection with the first electrode area 14 of neutral electrode 13 as well as a second neutral connection 27 for electrical connection with a second electrode area 15 of neutral electrode 13 are apparatus connections 20 of supply apparatus 11 in the embodiment.

If the supply apparatus 11 is exclusively configured for use with bipolar instruments 12b, one single working connection 21 is sufficient in modification to the illustrated embodiment. It is in addition possible to provide more than two working connections 21, 22, if the electrosurgical instrument 12 comprises more than two working electrodes.

The supply apparatus 11 is configured to supply the at least one working electrode 23 or 24, 25 of the connected electrosurgical instrument 12 with electrical energy. During treatment of tissue 16 a treatment current hereby flows through the treated biological tissue 16. When using a monopolar instrument 12a, the treatment current can flow from the working electrode 23 through the tissue 16 to the neutral electrode 13 and from there back to the supply apparatus 11. When using a bipolar instrument 12b, the treatment current flows between the two working electrodes 24, 25 through the tissue 16. In both cases a closed current circuit is established.

A block diagram of an embodiment of an operating circuit 30 of supply apparatus 11 is illustrated in FIG. 3. The operating circuit 30, according to FIG. 3, illustrates the important components and parts of the electrical circuit of supply apparatus 11, wherein additional other circuit parts can be present that are not illustrated in the operating circuit 30 according to FIG. 3.

The operating circuit 30 comprises a generator 31 that can be configured as alternating current source or alternating voltage source. Generator 31 an alternating current and/or an alternating voltage having alternating polarity is provided as generator voltage UG and/or generator current IG according to the example, wherein the frequency can be in the range of 300 kHz to 4.0 MHz. Dependent on the operating mode of supply apparatus 11 or the electrosurgical system 10 and the application, generator 31 can provide the generator voltage UG or the generator current IG, also at different frequencies.

As illustrated in FIG. 3, a connection of generator 31 is electrically connected with first working connection 21 via a first line 32 and generator 31 is electrically connected with its other terminal with second working connection 22 of supply apparatus 11 via a second line 33.

According to the example, the operating circuit 30 has a measurement signal source 34 for providing a measurement signal XM. The measurement signal source 34 can be a current source or a voltage source and accordingly can provide a measurement voltage UM and/or a measurement current IM as measurement signal XM. The measurement signal XM is an alternating current or alternating voltage signal having a measurement frequency fm, particularly with alternating polarity. The measurement frequency can be set to different measurement frequencies fm in a continuous manner or in steps, e.g. to a first measurement frequency f1, a second measurement frequency f2 and/or a third measurement frequency F3. The number of settable measurement frequencies fm can vary. In the embodiment the measurement frequency can be set to one or more measurement frequencies fm in the range of 1.0 Hz or 10 Hz or 100 Hz up to 1.0 MHz.

The measurement signal XM (e.g. measurement voltage UM) has an amplitude of maximum 1.0 V and in the embodiment of approximately 10 mV.

The measurement signal source 34 is electrically connected at one terminal to the first neutral connection 26 via a third line 35 and at the other terminal to the second neutral connection 27 via a fourth line 36. Thus, the measurement signal source 34 can create a current flow of a measurement current IM through a neutral electrode 13 connected to the neutral connections 26, 27.

The operating circuit 30 comprises in addition a measurement device 40. The measurement device 40 is configured to measure an impedance parameter P that describes an impedance Z between two selected apparatus connections 20 between which the measurement voltage UM applies. In the embodiment the impedance parameter P can describe a first impedance Z1 in a treatment current path B or a second impedance Z2 in a neutral current path N. The treatment current path B is the electrical connection between the first working connection 21 and the neutral connections 26, 27 via the monopolar instrument 12a and the tissue 16 or between the first working connection 21 and the second working connection 22 via the bipolar instrument 12b and the tissue 16. The neutral current path N is the electrical connection between the neutral connections 26, 27 via neutral electrode 13 and the patient.

The generator current or its fraction flowing through the treatment current path B comprising the instrument can also be denoted as working or treatment current.

If a measurement voltage UM is provided as measurement signal XM, a measurement current IM through the treatment current path B or the neutral current path N created thereby can be used as impedance parameter P. If vice versa a measurement current IM is impressed as measurement signal XM, a measurement voltage UM applied to the treatment current path B or the neutral current path N can be used as impedance parameter P. In the example illustrated in FIG. 3, the measurement current IM serves as impedance parameter P that can be measured, for example, based on a voltage occurring at a first measurement resistor 41 of measurement device 40 connected in series to the measurement signal source 34.

In the embodiment the measurement device 40 comprises in addition a frequency-dependent impedance circuit that is here configured as parallel oscillating circuit 44. The frequency-dependent impedance circuit and according to the example the parallel oscillating circuit 44 connects third line 35 with fourth line 36 electrically. In a preferred embodiment parallel oscillating circuit 44 can comprise a parallel inductance 42 and two series capacitors 43. Additional parts are optional, but not required. The values of the parts of the parallel oscillating circuit 44 can be dimensioned so that the oscillating circuit has a frequency-dependent impedance progress, as shown in FIG. 11 by way of example. The impedance progress is the absolute value of the impedance ZP of the parallel oscillating circuit 44 depending on the frequency f. The impedance progress has an impedance maximum ZPmax (absolute value) at a frequency that is denoted for sake of distinction as oscillating circuit frequency f0, which is significantly different from the generator frequency fg at which generator 31 provides the generator voltage UG or the generator current IG (can also be denoted as working current). In a preferred embodiment the oscillating circuit frequency f0 is at least about a factor 3 lower than the generator frequency fg. The frequency-dependent impedance circuit formed by parallel oscillating circuit 44 is in addition characterized in that it has a remarkably lower amount or absolute value of the impedance ZP compared to the impedance maximum ZPmax at the generator frequency fg, e.g. maximum 10% of the impedance maximum ZPmax.

Instead of the parallel oscillating circuit also other frequency-dependent impedance circuits having one or more local impedance maximum can be used that have at least one component having a frequency-dependent impedance absolute value, particularly at least one coil or impedance and/or at least one capacitor.

The measurement device 40 can measure other parameters in addition to the impedance parameter P, e.g. a first current I1 through the third line 35 and/or a second current I2 through the fourth line 36. For this purpose measurement device 40 can comprise a second measurement resistor 45 in third line 35 and a third measurement resistor 46 in fourth line 36. As an additional option, the measurement device 40 can be configured for measurement of a generator current IG that flows due to a generator voltage UG provided by generator 31. For example, a fourth measurement resistance 47 can be arranged in first line 32 for this purpose.

An evaluation unit 50 is part of the operating circuit 30 in the embodiment. The evaluation unit 50 is provided at least with the impedance parameter P, which is measured by measurement device 40. The impedance parameter P describes, as explained, the first impedance Z1 in the treatment current path B and/or the second impedance Z2 in the neutral current path N.

As an option also additional parameters or variables can be provided to the evaluation unit 50, which can be detected by measurement device 40, such as a first current I1 and/or the second current I2 and/or the generator current IG.

In addition, operating circuit 30 comprises a switch device 51 switchable between multiple switch conditions. The switch device 51 can comprise one or more controllable switches for this purpose, which can be respectively controlled by one assigned control signal. In the embodiment a first switch 52 controllable by a first control signal S1, a second switch 53 controllable by a second control signal S2, a third switch 54 controllable by a third control signal S3, a fourth switch 55 controllable by a fourth control signal S4, a fifth switch 56 controllable by a fifth control signal S5 as well as a sixth switch 57 controllable by a sixth control signal S6 are provided. The control signals S1-S6 are created in a control unit 58 of operating circuit 30. As schematically illustrated in FIG. 3, evaluation unit 50 and control unit 58 can be one common component or unit as an option.

For example, switches 52-57 can be configured as controllable semi-conductor switches (e.g. bipolar or field-effect transistors). It is clear that the switch device 51 can also have more or less than six controllable switches 52-57 in modification to the embodiment illustrated in FIG. 3. In the embodiment the switches 52-57 of switch device 51 are arranged as follows:

First switch 52 is arranged in a connection path between third line 35 and first neutral connection 26 and fourth line 36 or second neutral connection 27 and is able to connect in a low ohmic manner or to short-circuit the two neutral connections 26, 27.

The second switch 53 is connected with one terminal side of measurement signal source 34 and can electrically connect this terminal side of the measurement signal source in one switch position with fourth line 36 or second neutral connection 27, whereby this terminal side of the measurement signal source can be electrically connected in another switch position with first line 32 or first working connection 21. The terminal side of the measurement signal source 34 opposite the second switch 53 is electrically connected with third line 35 or first neutral connection 26.

Third switch 54 is arranged between first neutral connection 26 and one connection side of parallel oscillating circuit 44 in the first line 35. Fourth switch 55 is arranged between second neutral connection 27 and the other side of parallel oscillating circuit 44 in the second line 36. Third switch 54 and fourth switch 55 can establish or interrupt the electrical connection between parallel oscillating circuit 44 and the respectively assigned neutral connection 26 or 27 and the measurement signal source 34.

The fifth switch 56 is connected in series to the measurement signal source 34 on the side opposite second switch 53 of the measurement signal source 34 and can establish or interrupt an electrical connection between the measurement signal source 34 and second line 33 or second working connection 22.

Sixth switch 57 is arranged between fourth measurement resistor 47 and first working connection 21 and can establish or separate an electrical connection from generator 31 to the first working connection 21 and to second switch 53.

Control unit 58 can switch the switch device 51 between at least two different switch conditions, according to the example between a first switch condition C1 (FIG. 4), a second switch condition C2 (FIG. 5), a third switch condition C3 (FIG. 6), a fourth switch condition C4 (FIG. 7) and a fifth switch condition C5 (FIG. 8). The control of the switch device 51 can inter alia depend on the actual operating condition of supply apparatus 11, e.g. whether the supply apparatus 11 is cooperating with a monopolar or bipolar instrument 12 and/or whether an electrical power is provided at the at least one working electrode 23, 24, 25 for treatment of tissue 16 or whether a treatment pause without provision of such an electrical power at the at least one working electrode 23, 24, 25 is present.

By the different switch conditions C1-C5, the evaluation unit 50 can carry out different evaluation tasks.

In the following, the switch conditions C1-C5, which switch device 51 can take in the embodiment are explained based on FIGS. 4-7, whereby in FIGS. 4-7 only the essential parts of operating circuit 30 are illustrated in simplified manner.

The first switch condition C1 is provided for the use of a monopolar instrument 12a and the neutral electrode 13. In the first switch condition C1 first switch 52, third switch 54, fourth switch 55 and fifth switch 56 are in their non-conducting condition. The second switch 53 connects the measurement signal source 34 with second neutral connection 27. The neutral current path N is the current path between first neutral connection 26 and second neutral connection 27, which is formed by neutral electrode 13 and tissue 16 and is illustrated in the equivalent circuit diagram by second impedance Z2. The neutral current path N is connected via third line 35 and fourth line 36 with measurement signal source 34 forming a closed current circuit.

If measurement signal source 34 provides a measurement voltage UM, a measurement current IM flows through neutral current path N, which can be measured by a measurement device 40 and can be transmitted as impedance parameter P to the evaluation unit 50. In the evaluation unit 50 it can be checked or monitored whether second impedance Z2 corresponds to a test criterion that characterizes a sufficiently good conductance between neutral electrode 13 and the patient. In this manner an electrical conductance between neutral electrode 13 and the patient, that is necessary for treatment of the patient, can be monitored. An incorrectly attached neutral electrode 13 and/or a detachment of neutral electrode 13 during treatment can be recognized. Thereby too high current densities within the tissue adjoining the neutral electrode 13 can be avoided that could result in tissue damages. If the second impedance Z2 of neutral current path N determined based on the impedance parameter P or the measurement current IM does not fulfill the predefined test criterion, a respective message can be output to the user of the electrosurgical system 10 and/or the further operation and for example the supply of the at least one working electrode 23 or 24, 25 with electrical energy can be inhibited.

The second switch condition C2 is illustrated in FIG. 5. The second switch condition C2 is also used in an electrosurgical system 10 having a monopolar instrument 12a and a neutral electrode 13. In the second switch condition C2 the first switch 52 is in its conducting condition and connects the two neutral connections 26, 27 in low ohmic manner. The second switch 53 is in a switch condition in which it electrically connects the measurement signal source 34 on one side with the neutral connections 26, 27 and on the other side with the first working connection 21. The current circuit is closed via the monopolar instrument 12a and its working electrode 23, the tissue 16 as well as the neutral electrode 13 connected to the neutral connections 26, 27 (treatment current path B for use of monopolar instrument 12a).

In the second switch condition C2 the measurement signal source 34 can provide a measurement voltage UM as measurement signal XM so that a measurement current IM flows through the treatment current path B. The treatment current path B is characterized by first impedance Z1 that particularly depends on the condition and on the type of tissue 16 with which the working electrode 23 of monopolar instrument 12a is in electrically conducting contact. The measurement current IM through the treatment current path B is characteristic for the first impedance Z1 and can be evaluated as impedance parameter P in the evaluation unit 50. The evaluation unit 50 can conclude first impedance Z1 based on the measurement current IM used as impedance parameter P and can therefrom determine a condition and/or a type of the treated tissue 16.

During a measurement with activated measurement signal source 34 in the first switch condition C1 and/or in the second switch condition C2 generator 31 is turned off and sixth switch 57 is opened so that neither a generator voltage UG nor a generator current IG are provided and generator 31 is galvanically not connected with the measurement signal source. In doing so, an interference of the measurement is avoided.

The third switch condition C3 is schematically shown in FIG. 6. In the third switch condition C3 first switch 52 and fifth switch 56 are in non-conducting condition. Third switch 54 and fourth switch 55 are in their conducting condition respectively. The second switch 53 connects the measurement signal source 34 with second neutral connection 27.

In the third switch condition C3 tissue 16 of a patient is treated by a monopolar instrument 12a. The generator 31 is active and provides a generator voltage UG and/or a generator current IG, so that an electrical power for treatment of the tissue 16 is available at the working electrode 23 of the monopolar instrument 12a. During treatment a current flows through the treatment current path B between first working connection 21 and neutral connections 26, 27, which is separated in a first current I1 in the third line 35 and a second current I2 in fourth line 36. By the measurement device 51, the two currents I1, I2 can be compared with one another in order to recognize inequalities and asymmetries that can be caused, for example, due to a neutral electrode 13 incorrectly arranged on the patient. For this purpose one or more characteristic current parameters of the currents I1, I2 can be compared with one another, such as an amplitude and/or an absolute value and/or a phase position.

In the third switch condition C3 in addition a measurement signal XM (e.g. measurement voltage UM) is provided by the measurement signal source 34 during an application of generator current IG to the tissue 16, whereby a measurement current IM flows through the neutral current path N, which can be measured by measurement device 40 and can be transmitted to the evaluation unit 50 as impedance parameter P. The measurement signal XM or the measurement voltage UM is thereby provided at a measurement frequency fm that sufficiently distinguishes from the generator frequency fg of generator current IG. Preferably the measurement frequency fm of measurement signal XM or measurement voltage UM is approximately equal to the oscillating circuit frequency f0 at which the parallel oscillating circuit 44 has its impedance maximum ZPmax. For the measurement current IM parallel oscillating circuit 44 represents a resistance having high impedance parallel to the second impedance Z2 of neutral electrode 13, whereby the impedance of the neutral electrode can be very accurately determined based on the measured impedance parameter P. For the generator current IG the parallel oscillating circuit 44 establishes a low ohmic connection between the two neutral connections 26, 27 and thus an electrical connection to generator 31 via third line 35 and fourth line 36.

Different to the switch conditions C1-C3 described so far, fourth switch condition C4 (FIG. 7) refers to an electrosurgical system 10 having a bipolar instrument 12b. In the fourth switch condition C4 first switch 52, third switch 54, fourth switch 55 as well as sixth switch 57 are in their non-conducting condition. The fifth switch 56 is, however, in its conducting condition. The second switch 53 connects the measurement signal source 34 with first working connection 21 or first line 32. The measurement signal source 34 is thus connected between the two working connections 21, 22, the generator 31 is separated from the measurement of sixth switch 57. A measurement voltage UM can thus be applied to the treatment current path B, so that a measurement current flow, which can be evaluated in the evaluation unit 50 as impedance parameter P. The impedance parameter P describes in this case the first impedance Z1 of treatment current path B, which is substantially characterized by the tissue 16 with which first working electrode 24 and second working electrode 25 of bipolar instrument 12b are in electrically conducting contact. Based on the impedance parameter P or the first impedance Z1 characterized thereby, the condition and/or the type of the tissue 16 can be determined in the evaluation unit 50.

Analog to the switch condition C4 the fifth switch condition C5 (FIG. 8) also refers to an electrosurgical system 10 having a bipolar instrument 12b. In this fifth switch condition C5, fifth switch 56 is in its non-conducting condition and thus separates the measurement signal source 34 from second working connection 22. The sixth switch 57 is in its conducting condition in the fifth switch condition C5 and thereby closes the current circuit from generator 31 via the treatment current path B (through first working connection 21 and a bipolar instrument 12b, the tissue 16 and the second working connection 22). This fifth switch condition C5 allows the treatment of tissue 16 in bipolar operation.

In the fifth switch condition C5 the measurement signal source can be configured or controlled so that it does not create a measurement signal XM.

In all switch conditions C1-C5 the result of the evaluation can be used in order to automatically influence the operation of supply apparatus 11 and/or in order to provide information to the user by a suitable user interface, which can be output, for example optically and/or acoustically. For example, the user can be informed about the condition and/or the type of the treated tissue 16. Depending on the condition and/or type of tissue, also electrical power and/or the frequency of generator 31 and/or other settings of the electrosurgical system 10 and particularly supply apparatus 11 can be adjusted or modified. If the electrosurgical system 10 has a monopolar instrument 12a with a neutral electrode 13 in addition the correct abutment of neutral electrode 13 on the patient can be checked and/or monitored during treatment.

Preferably during operation of the electrosurgical system 10 in one or more switch conditions, particularly first switch condition C1 and/or second switch condition C2 and/or fourth switch condition C4 and/or fifth switch condition C5 an alternating current or an alternating voltage is not concurrently created by generator 31 and by measurement signal source 34. Rather the creation of a measurement signal XM and the measurement of the impedance parameter P characterizing the impedance Z1, Z2 is carried out in temporal periods in which generator 31 is inactive and thus does not provide an electrical power (generator voltage UG and/or generator current IG), as schematically illustrated in FIG. 9. As shown in FIG. 9, the current flow of a measurement current IM is only caused by activating the measurement signal source 34, if no treatment of the tissue 16 is carried out by a generator current IG created by generator 31. In other words, treatment periods Pt during which a generator current IG or a treatment current flows through the treatment current path B do not overlap with measurement periods Pm during which a measurement current IM flows through the neutral current path N or the treatment current path B in the one or more switch conditions, particularly the first switch condition C1 and/or second switch condition C2 and/or fourth switch condition C4 and/or fifth switch condition C5.

It is also apparent from FIG. 9 that measurement frequency fm may vary with which measurement signal XM is created. Only exemplarily three different measurement frequencies fm=f1, f2, f3 are shown in FIG. 9 during different measurement periods Pm. The number of different measurement frequencies fm can vary.

It is in addition apparent from FIG. 9 that measurement periods Pm having different measurement frequencies fm=f1, f2, f3 can adjoin directly or can be separated from one another by a treatment period Pt.

In the third switch condition C3, different to other switch conditions, according to the example the first switch condition C1 and/or second switch condition C2 and/or fourth switch condition C4 and/or fifth switch condition C5, a concurrent activation of measurement signal source 34 and generator 31 is possible. For this purpose, the measurement signal XM is created at a measurement frequency fm that remarkably distinguishes from generator frequency fg and is preferably approximately equal to the oscillating circuit frequency f0. As explained, the parallel oscillating circuit 44 represents a parallel resistance having a high absolute value of the impedance ZP in the range of the impedance maximum ZPmax for the measurement current IM while it represents a low ohmic connection for the working current IG at the generator frequency fg. This allows the evaluation of the impedance parameter P at the measurement frequency fm=f0, also during treatment of tissue 16 with a monopolar instrument 12a. In this manner a detachment of neutral electrode 13 can also be monitored during treatment or activation of generator 31 and the monopolar instrument 12a, for example.

By way of example, it is illustrated in FIG. 10 that the treatment period Pt and a measurement period Pm can temporarily overlap, i.e. that a concurrent activation of generator 31 and measurement signal source 34 occurs. It can be recognized that the measurement frequency fm=f0, with which the measurement signal XM is created, distinguishes remarkably from the generator frequency fg. After termination of an activation of generator 31, measurement signal XM can again be measured at another frequency that can be, for example, similar or equal to the generator frequency fg, as illustrated in FIG. 10 by f3, in that the switch device 51 takes switch condition C1 or C2, for example.

In an embodiment the measurement frequency fm can be varied during activation of generator 31 in a small frequency range around the oscillating circuit frequency f0 of impedance maximum ZPmax of impedance ZP of parallel oscillating circuit 44, in order to exactly determine the frequency at which the impedance maximum ZPmax occurs.

An exemplary impedance progress of impedance ZP of parallel oscillating circuit 44 over a frequency range can be seen in FIG. 11. It is apparent that parallel oscillating circuit 44 is high ohmic at oscillating circuit frequency f0 and comprises its impedance maximum ZPmax there. The impedance ZP decreases originating from the oscillating circuit frequency f0 with increasing and decreasing frequency f and is low ohmic at generator frequency fg.

The invention refers to a supply apparatus 11 for an electrosurgical system 10 as well as an electrosurgical system 10 comprising a supply apparatus according to the invention. The electrosurgical system 10 can, in addition, comprise a monopolar instrument 12a and a neutral electrode 13 or a bipolar instrument 12b. The supply apparatus 11 has at least one working connection 21 for one working electrode 23, 24, 25 of an electrosurgical instrument 12 respectively as well as a first neutral connection 26 and a second neutral connection 27 for a neutral electrode 13. The supply apparatus 11 has a generator 31 by which an electrical power can be provided for the electrosurgical instrument 12 for treatment of biological tissue 16. In addition, supply apparatus 11 has a measurement signal source 34 that provides a measurement signal XM in form of an alternating voltage and/or an alternating current. An impedance parameter P characterizing an impedance Z1, Z2 resulting from the measurement signal XM can be measured by a measurement device 40 of supply apparatus 11 and can be provided to an evaluation unit 50 of supply apparatus 11 for evaluation. The supply apparatus 11 has, in addition, a switch device 51 that can be switched between multiple switch conditions C1-C5. In the different switch conditions C1-C5 different evaluation functions can be realized by the evaluation unit 50: The measurement signal source 34 can apply a measurement signal to a treatment current path B at a working connection 21 as well as to a neutral current path N between the neutral connections 26, 27. In doing so, a treated tissue 16 can be analyzed and also a contact between the neutral electrode 13 and the patient can be checked and monitored by the measurement signal XM.

The invention claimed is:

1. A supply apparatus for an electrosurgical system comprising:
    at least two neutral connections for a neutral electrode (13) and at least one working connection for one working electrode of an electrosurgical instrument respectively,
    a generator for providing a generator voltage (UG) or a generator current (IG) at a generator frequency (fg),
    a measurement signal source for providing a measurement signal (XM) alternating with a measurement frequency (fm),
    a measurement device for measurement of an impedance parameter (P) that describes an impedance (Z1, Z2) between two apparatus connections to which the measurement signal (XM) is provided,
    a switch device that can be switched between multiple switch conditions (C1, C2, C3, C4, C5), which electrically connects the measurement signal source with the two neutral connections and disconnects the measurement signal source electrically from the at least one working connection in a first switch condition (C1) and which electrically connects the measurement signal source with at least one of the working connections in a second switch condition, and
    an evaluation unit that is communicatively connected with the measurement device and configured for evaluation of the measured impedance parameter (P).

2. The supply apparatus according to claim 1, comprising a first working connection for connection of a working electrode of a monopolar instrument.

3. The supply apparatus according to claim 1, comprising a first working connection for connection of a first working electrode and a second working connection for connection of a second working electrode of a bipolar instrument.

4. The supply apparatus according to claim 1, wherein the measurement signal source is configured to provide the measurement signal (XM) at multiple measurement frequencies (fm) that are different from one another.

5. The supply apparatus according to claim 1, wherein in the first switch condition (C1) the evaluation unit is configured to check an electrical contact between a neutral electrode connected to the two neutral connections and a patient based on the measured impedance parameter (P).

6. The supply apparatus according to claim 1, comprising a first neutral connection for connection of an electrically conductive first electrode area of a neutral electrode and a second neutral connection for connection of an electrically conducting second electrode area of the neutral electrode.

7. The supply apparatus according to claim 1, wherein in the second switch condition (C2) the evaluation unit is configured to determine, based on the measured impedance parameter (P), a tissue condition and/or a tissue type of tissue with which a working electrode of an electrosurgical instrument connected to the at least one working connection is in electrically conducting contact.

8. The supply apparatus according to claim 1, wherein the switch device disconnects the generator electrically from the measurement signal source in the first switch condition (C1) and in the second switch condition (C2).

9. The supply apparatus according to claim 1, wherein the generator is configured or controlled so that the generator does not provide a generator voltage (UG) or a generator current (IG), if the measurement signal source provides a measurement signal (XM) to the switch device in the first switch condition and/or the second switch condition (C2).

10. The supply apparatus according to claim 1, wherein in the second switch condition (C2) the switch device electrically connects the measurement signal source on one side with the at least one working connection and on an other side with the two neutral connections.

11. The supply apparatus according to claim 1, wherein in the third switch condition (C3) the switch device electrically connects the generator on one side with the at least one working connection and on an other side with the neutral connections.

12. The supply apparatus according to claim 11, wherein in the third switch condition (C3) the evaluation unit is configured to check a first current (I1) at the first neutral connection and a second current (I2) at the second neutral connection created by the generator current (IG).

13. The supply apparatus according to claim 11, wherein in the third switch condition (C3) the switch device electrically connects a frequency-dependent impedance circuit, particularly a parallel oscillating circuit, with the measurement signal source.

14. The supply apparatus according to claim 1, wherein in a third switch condition (C3) the measurement signal source is configured or controlled, so that the measurement signal source creates a measurement signal (XM) at the measurement frequency (fm), which is different from the generator frequency (fg).

15. The supply apparatus according to claim 14, wherein in the third switch condition (C3) the measurement signal source is configured or controlled, so that the measurement frequency (fm) of the measurement signal (XM) varies in a frequency range in order to determine a frequency at which a frequency-dependent impedance circuit comprises an impedance maximum (ZPmax).

16. The supply apparatus according to claim 1, comprising a first working connection and a second working connection, wherein the switch device electrically connects the measurement signal source on one side with the first working connection and on an other side with the second working connection in a fourth switch condition (C4).

17. The supply apparatus according to claim 1, comprising a first working connection and a second working connection, wherein the switch device electrically connects the generator on one side with the first working connection and on the other side with the second working connection and disconnects the measurement signal source from first working connection and from second working connection in a fifth switch condition (C5).

18. An electrosurgical system comprising the supply apparatus of claim 1 and further comprising a bipolar instrument or a monopolar instrument.

*     *     *     *     *